(12) United States Patent
Asiyanbola

(10) Patent No.: US 12,383,265 B1
(45) Date of Patent: Aug. 12, 2025

(54) ENDOSTAPLER, PARTICULARLY FOR USE IN OPERATIONS ON THE PANCREAS

(71) Applicant: Bolanle Asiyanbola, Hermitage, TN (US)

(72) Inventor: Bolanle Asiyanbola, Hermitage, TN (US)

(73) Assignee: Bolanle Asiyanbola, Hermitage, TN (US)

( * ) Notice: Subject to any disclaimer, the term of this patent is extended or adjusted under 35 U.S.C. 154(b) by 0 days.

(21) Appl. No.: 18/750,759

(22) Filed: Jun. 21, 2024

(51) Int. Cl.
| | | |
|---|---|---|
| *A61B 17/072* | (2006.01) | |
| *A61B 17/068* | (2006.01) | |
| A61B 17/04 | (2006.01) | |
| A61B 17/10 | (2006.01) | |
| A61B 17/295 | (2006.01) | |
| A61B 34/30 | (2016.01) | |

(52) U.S. Cl.
CPC .......... *A61B 17/072* (2013.01); *A61B 17/068* (2013.01); *A61B 17/07207* (2013.01); *A61B 17/04* (2013.01); *A61B 17/0491* (2013.01); *A61B 2017/07214* (2013.01); *A61B 2017/07257* (2013.01); *A61B 2017/07285* (2013.01); *A61B 17/105* (2013.01); *A61B 17/295* (2013.01); *A61B 34/30* (2016.02)

(58) Field of Classification Search
CPC .............. A61B 17/068; A61B 17/0682; A61B 17/0686; A61B 17/072; A61B 17/07207; A61B 17/105; A61B 17/29; A61B 17/295; A61B 17/04; A61B 17/0469; A61B 17/0491; A61B 2017/07214; A61B 2017/07271; A61B 2017/07257; A61B 2017/07285; A61B 34/30; A61B 34/71; A61B 90/08

USPC ..... 227/19, 175.1, 176.1, 180.1; 606/1, 139, 606/219

See application file for complete search history.

(56) References Cited

U.S. PATENT DOCUMENTS

| | | | | |
|---|---|---|---|---|
| 5,484,451 A | * | 1/1996 | Akopov ................. | A61B 17/04 227/176.1 |
| 5,540,375 A | * | 7/1996 | Bolanos ............... | A61B 17/072 227/19 |
| 5,571,285 A | * | 11/1996 | Chow .................. | A61B 17/105 606/75 |
| 5,833,695 A | * | 11/1998 | Yoon ................ | A61B 17/07207 227/176.1 |
| 7,097,089 B2 | | 8/2006 | Marczyk | |

(Continued)

FOREIGN PATENT DOCUMENTS

WO    WO 2023/114525 A1    6/2023

*Primary Examiner* — Scott A Smith
(74) *Attorney, Agent, or Firm* — Craig Fieschko; DeWitt LLP

(57) ABSTRACT

An endostapler has a stapler body with distally-situated first and second stapler units, each of which may pivot from a stowed position oriented parallel to the stapler body to a deployed position oriented at an angle to the stapler body. Each stapler unit may open to receive tissue, and close upon the tissue to cut and staple it. When stapling, parallel adjacent rows of staples are applied adjacent the cut, and the staples are offset between the rows such that the staples in each row are adjacent the spaces between staples in the adjacent row. A third stapler unit has jaws situated about the first and second stapler units, and may close upon and staple tissue situated between the deployed first and second stapler units.

20 Claims, 11 Drawing Sheets

(56) References Cited

U.S. PATENT DOCUMENTS

| | | |
|---|---|---|
| 7,143,924 B2 | 12/2006 | Scirica et al. |
| 7,398,908 B2 | 7/2008 | Holsten et al. |
| 7,401,721 B2 | 7/2008 | Holsten et al. |
| 7,407,075 B2 | 8/2008 | Holsten et al. |
| 7,472,816 B2 | 1/2009 | Holsten et al. |
| 7,588,174 B2 | 9/2009 | Holsten et al. |
| 7,635,074 B2 | 12/2009 | Olson et al. |
| 7,753,246 B2 | 7/2010 | Scirica |
| 7,828,189 B2 | 11/2010 | Holsten et al. |
| 7,837,079 B2 | 11/2010 | Holsten et al. |
| 7,845,535 B2 | 12/2010 | Scircia |
| 7,866,525 B2 | 1/2011 | Scircia |
| 7,896,214 B2 | 3/2011 | Farascioni |
| 7,967,178 B2 | 6/2011 | Scirica et al. |
| 7,988,028 B2 | 8/2011 | Farascioni et al. |
| 7,997,469 B2 | 8/2011 | Olson et al. |
| 8,011,555 B2 | 9/2011 | Tarinelli et al. |
| 8,033,438 B2 | 10/2011 | Scirica |
| 8,066,166 B2 | 11/2011 | Demmy et al. |
| 8,157,149 B2 | 4/2012 | Olson et al. |
| 8,215,532 B2 | 7/2012 | Marczyk |
| 8,225,979 B2 | 7/2012 | Farascioni et al. |
| 8,292,146 B2 | 10/2012 | Holsten et al. |
| 8,336,753 B2 | 12/2012 | Olson et al. |
| 8,360,294 B2 | 1/2013 | Scirica |
| 8,360,298 B2 | 1/2013 | Farascioni et al. |
| 8,365,972 B2 | 2/2013 | Aranyi et al. |
| 8,371,492 B2 | 2/2013 | Aranyi et al. |
| 8,397,972 B2 | 3/2013 | Kostrzewski |
| 8,403,195 B2 | 3/2013 | Beardsley et al. |
| 8,408,440 B2 | 4/2013 | Olson et al. |
| 8,418,906 B2 | 4/2013 | Farascioni et al. |
| 8,496,153 B2 | 7/2013 | Demmy et al. |
| 8,573,460 B2 | 11/2013 | Cappola |
| 8,579,178 B2 | 11/2013 | Holsten et al. |
| 8,631,989 B2 | 1/2014 | Aranyi et al. |
| 8,636,192 B2 | 1/2014 | Farascioni et al. |
| 8,684,247 B2 | 4/2014 | Scirica et al. |
| 8,770,458 B2 | 7/2014 | Scirica |
| 8,777,082 B2 | 7/2014 | Scirica |
| 11,806,007 B2 * | 11/2023 | Börner ............... A61B 17/0625 |
| 11,806,015 B2 * | 11/2023 | Wixey .................. A61B 90/08 |
| 12,029,426 B2 * | 7/2024 | Millman .......... A61B 17/07207 |
| 2003/0135204 A1 * | 7/2003 | Lee ......................... B25J 9/104 |
| | | 606/1 |
| 2011/0251613 A1 * | 10/2011 | Guerra ................. A61B 17/295 |
| | | 606/52 |
| 2016/0235489 A1 * | 8/2016 | Gombert ............... B25J 9/1689 |
| 2017/0079710 A1 * | 3/2017 | Deville ............. A61B 18/1445 |
| 2017/0231653 A1 * | 8/2017 | Kapadia ................ A61B 34/71 |
| | | 606/208 |
| 2018/0168637 A1 * | 6/2018 | Harris .................. A61B 17/072 |
| 2019/0083086 A1 * | 3/2019 | Klaffenböck ...... A61B 17/0491 |
| 2019/0133571 A1 * | 5/2019 | Racenet ................. A61B 17/29 |
| 2022/0015823 A1 * | 1/2022 | Wilson ............... A61B 18/1445 |
| 2022/0061836 A1 * | 3/2022 | Parihar ............. A61B 17/0686 |

\* cited by examiner

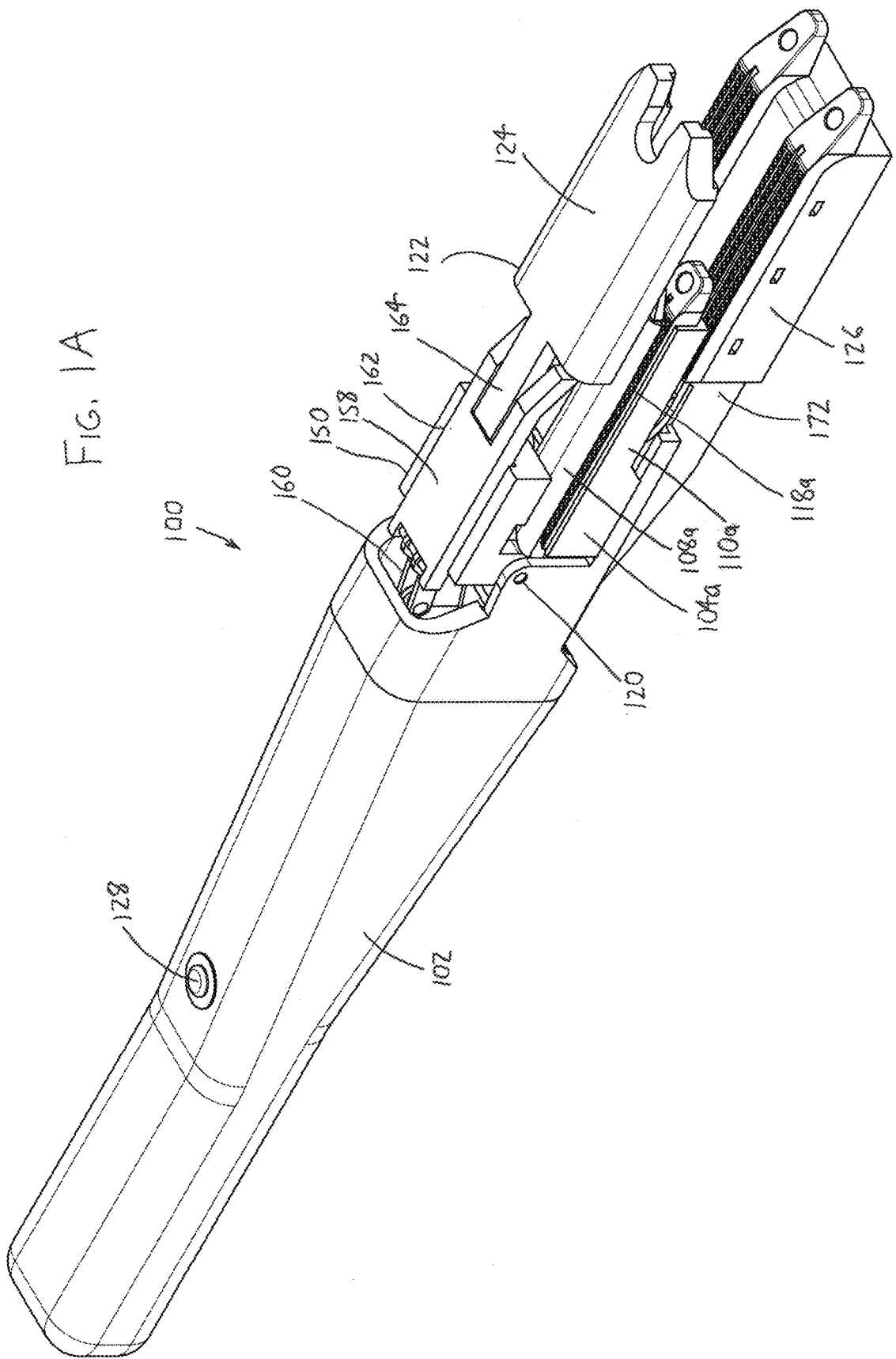

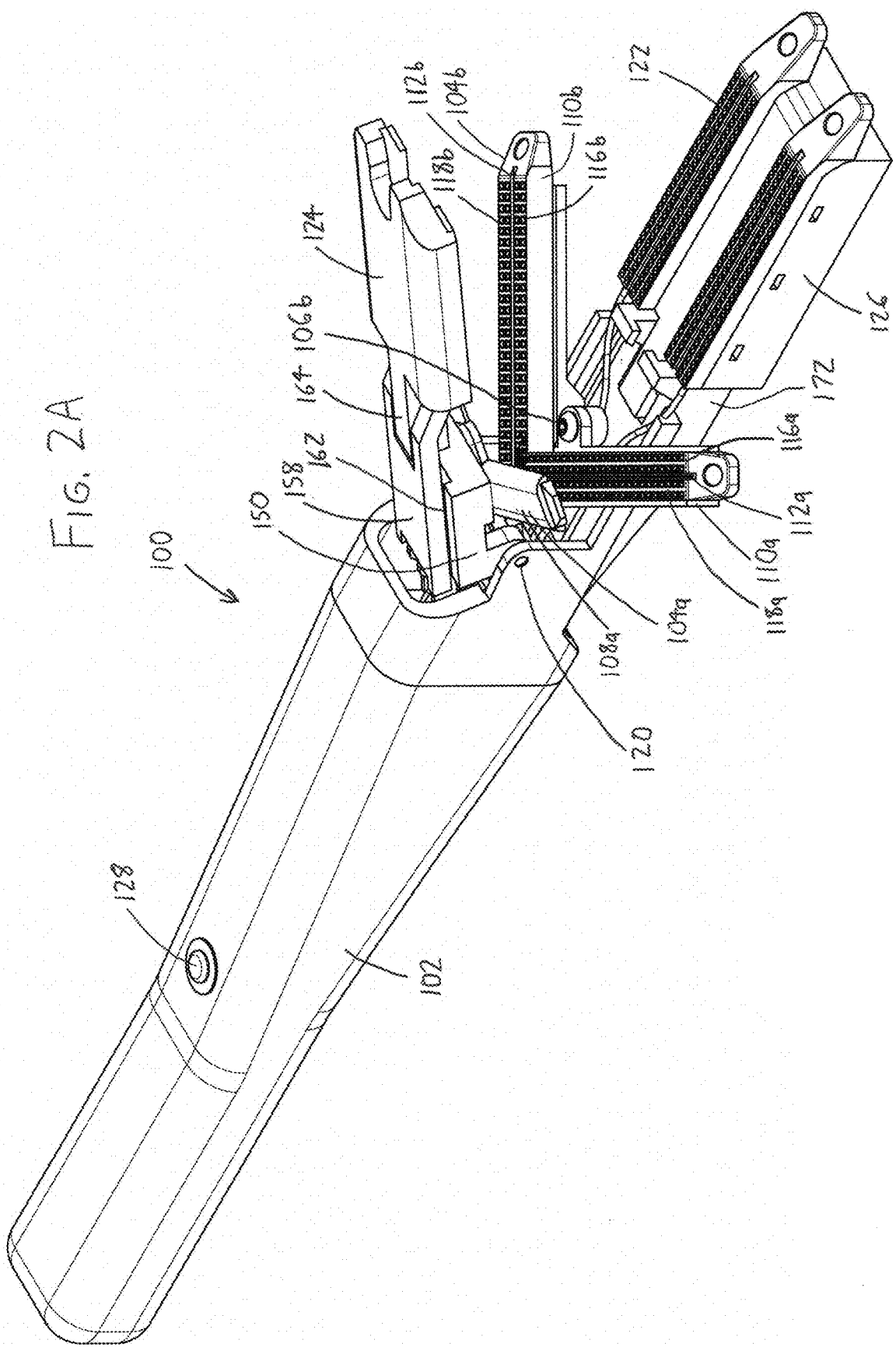

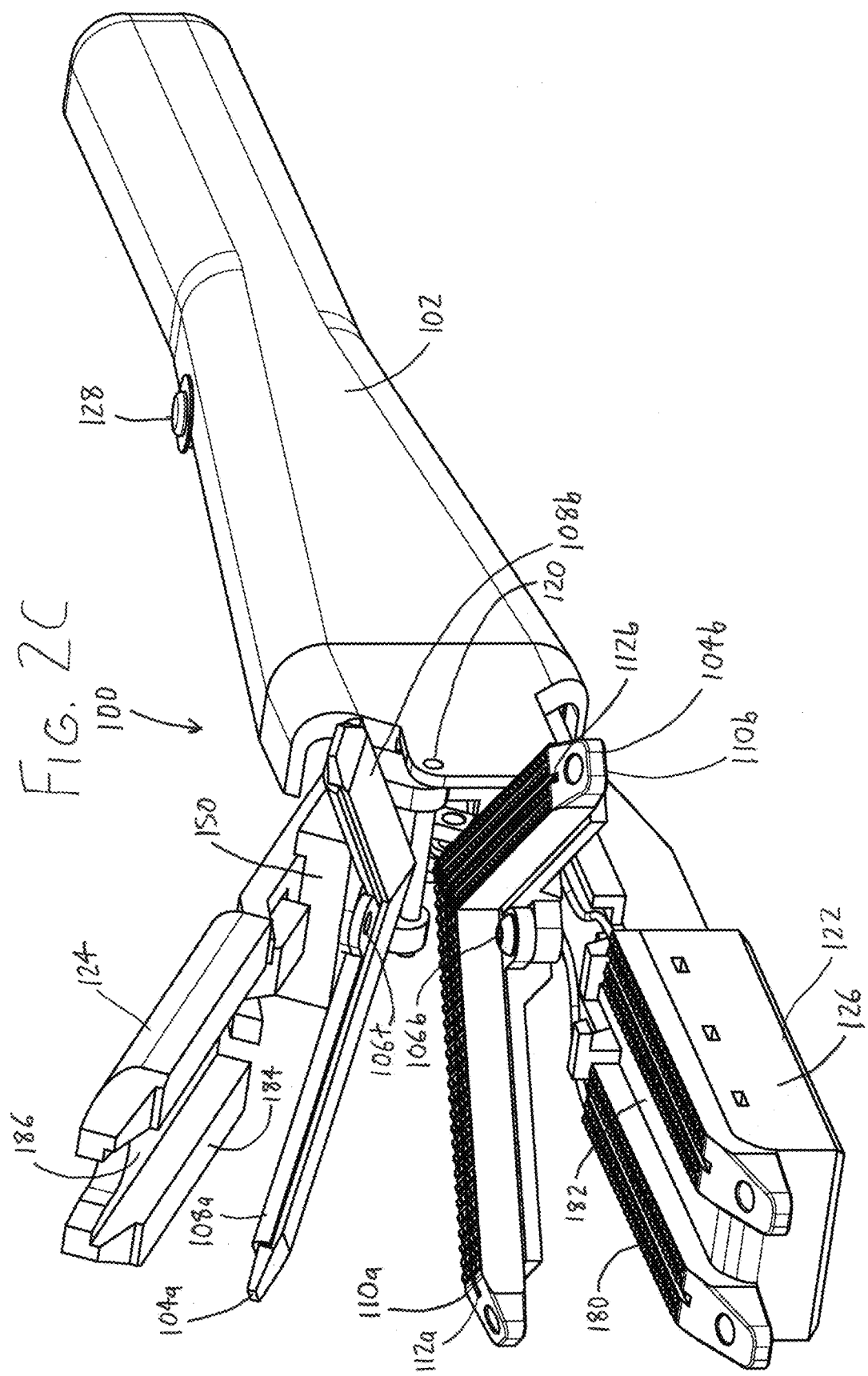

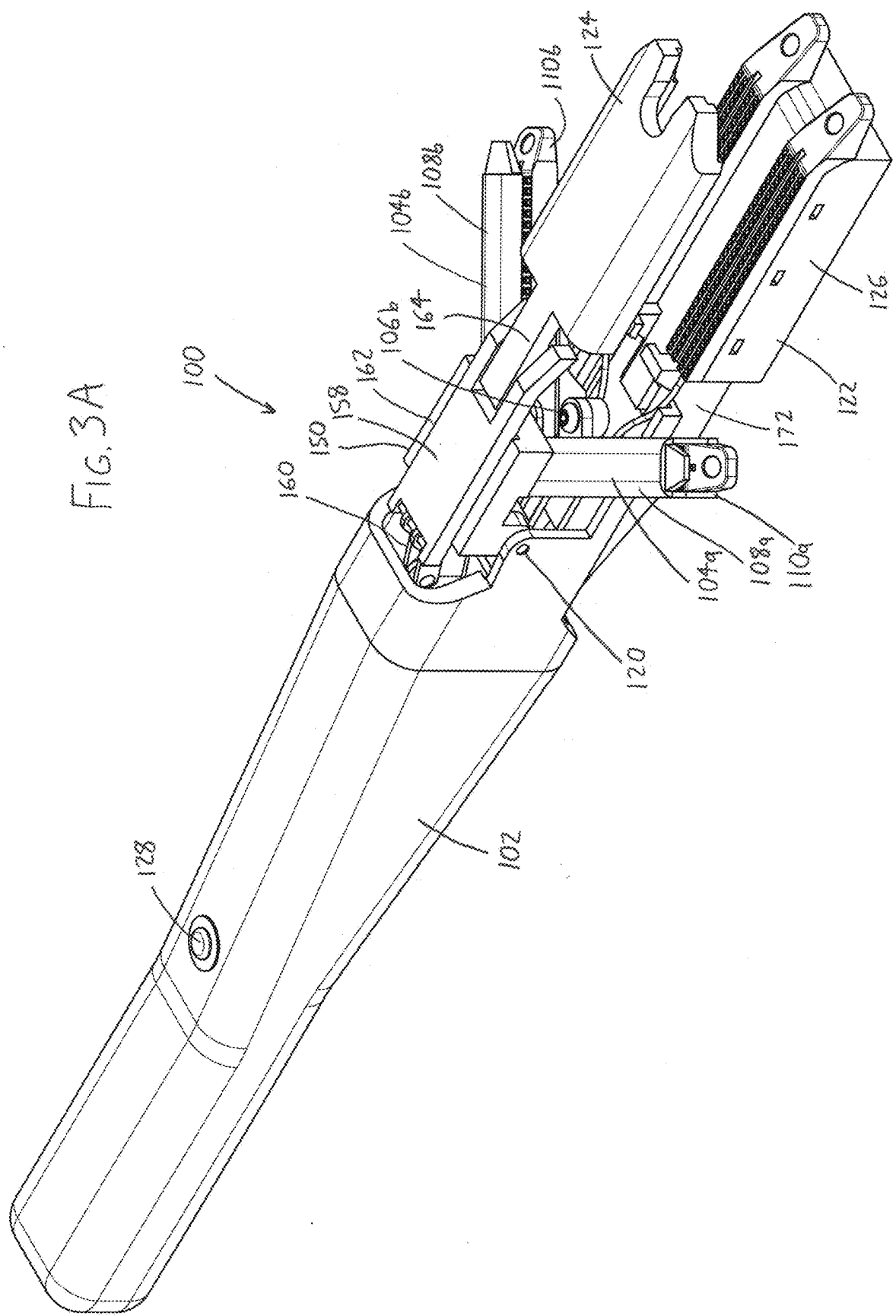

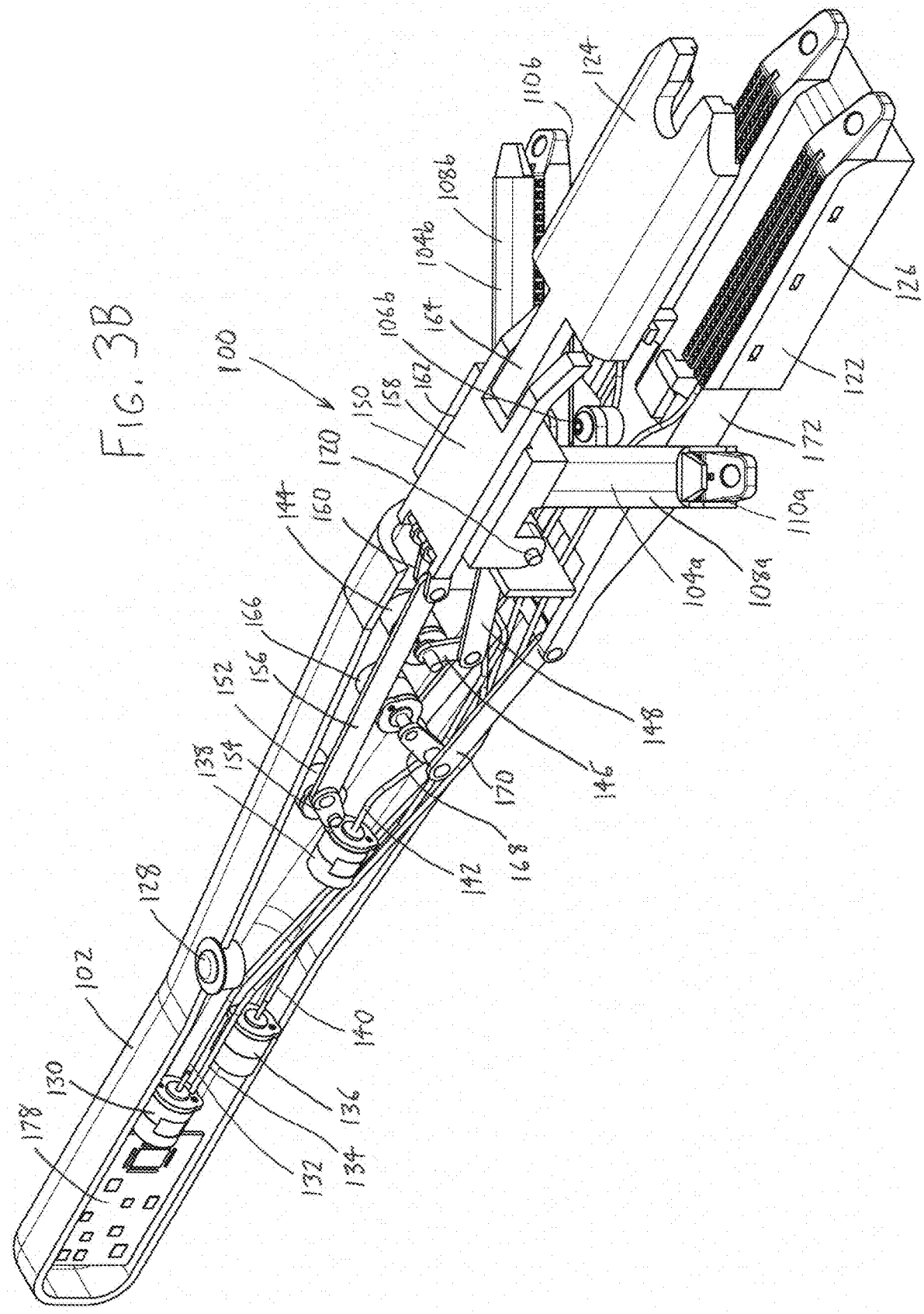

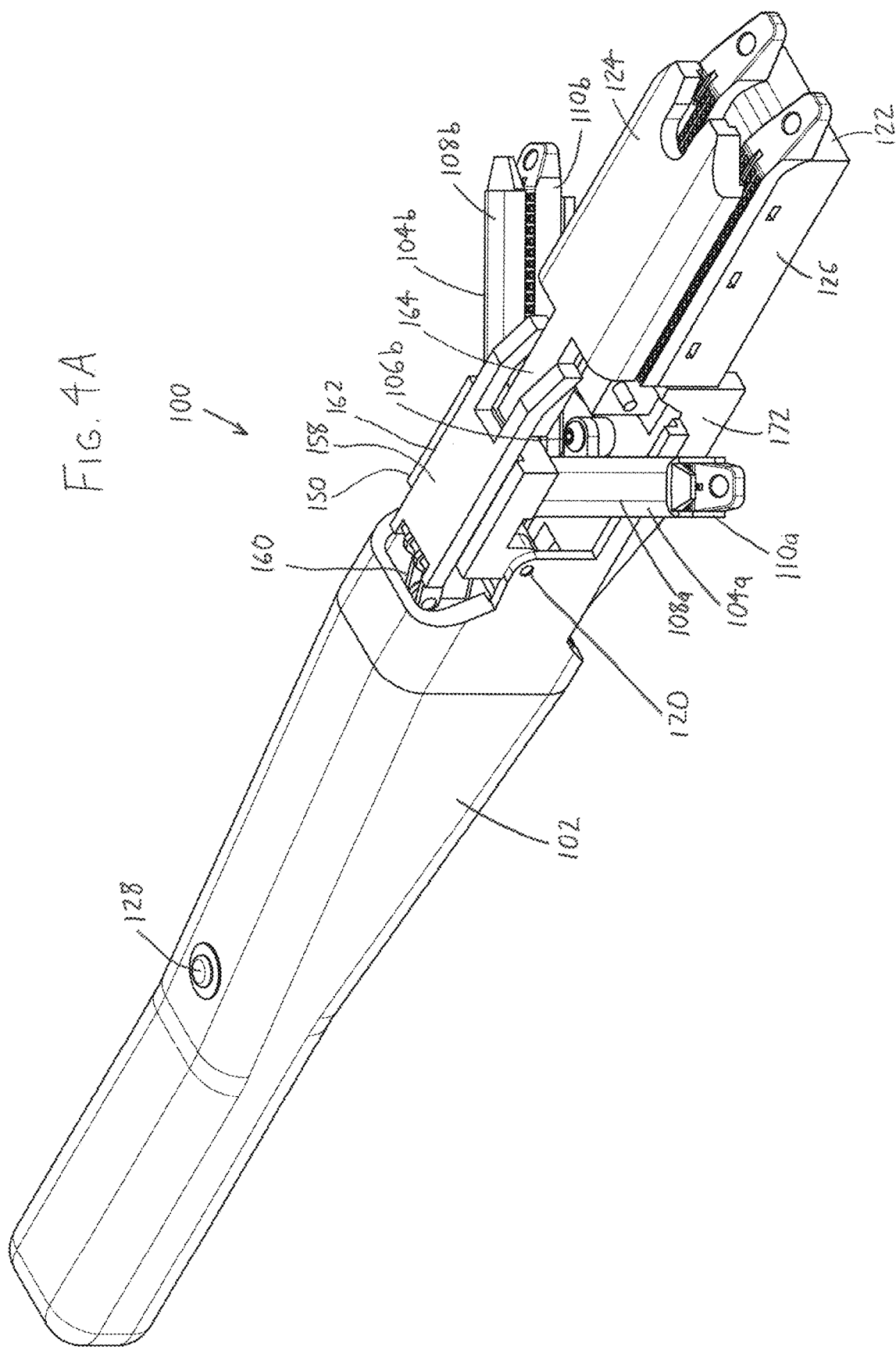

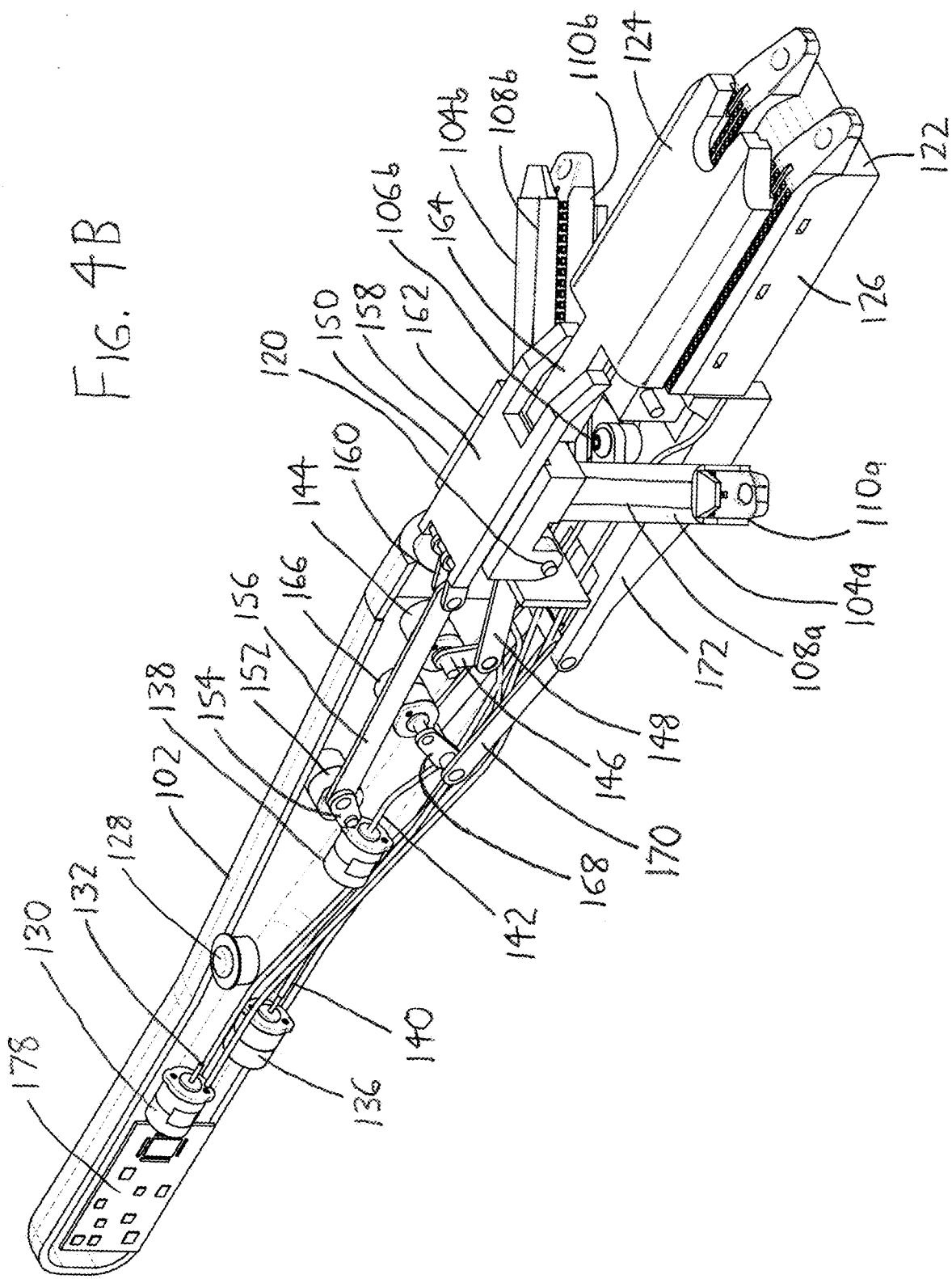

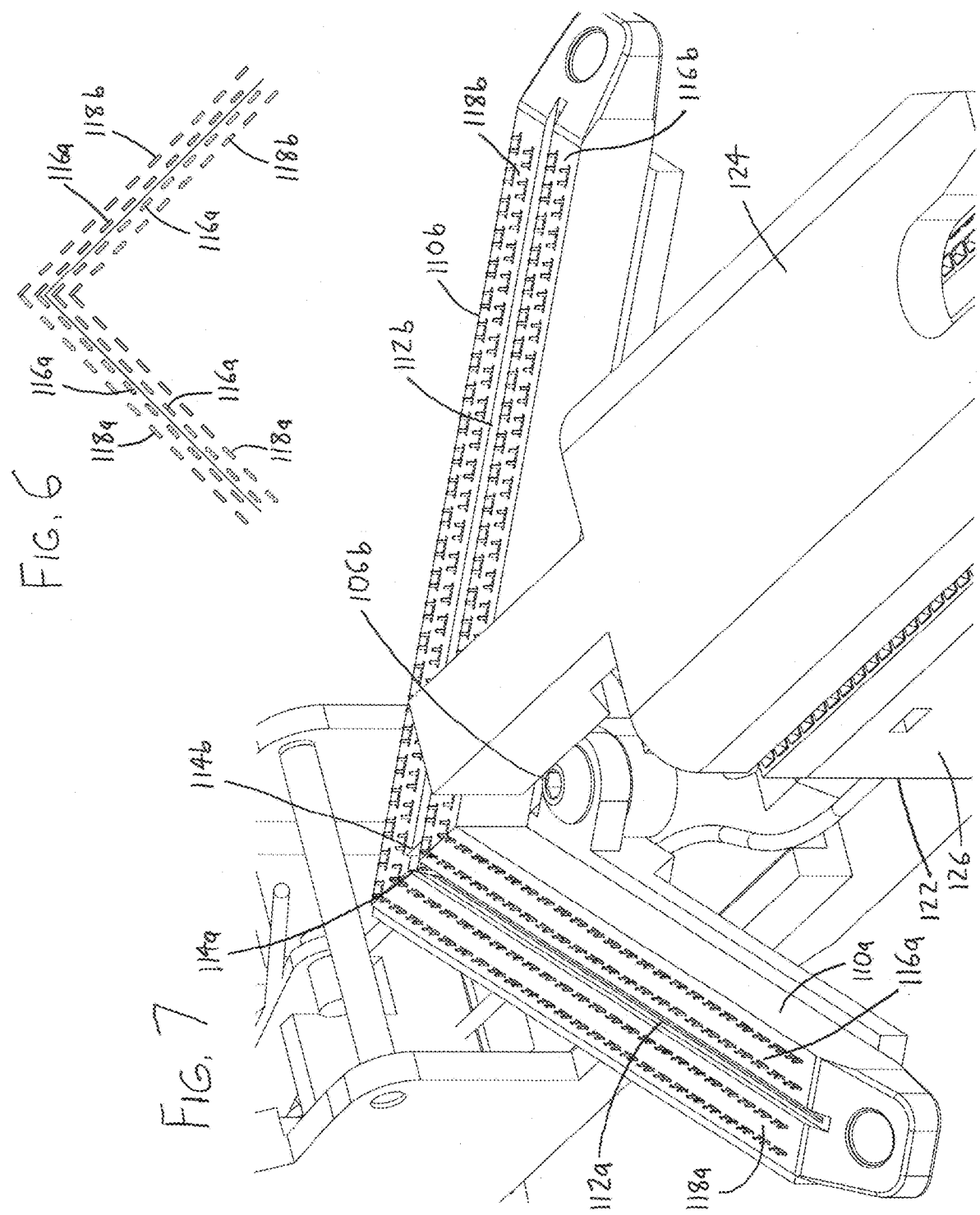

ENDOSTAPLER, PARTICULARLY FOR USE IN OPERATIONS ON THE PANCREAS

FIELD OF THE INVENTION

This document concerns an invention relating generally to surgical staplers, and more specifically to endoscopic cutting staplers.

BACKGROUND OF THE INVENTION

A surgical cutting endoscopic stapler, often referred to as simply an endostapler, is a device having jaws which can be inserted within a body to fit around an anatomical structure. The endostapler can be actuated to have the jaws clamp down on the structure, with the jaws simultaneously cutting and stapling the structure. Endostapler jaws often provide two parallel rows of staplers, whereby two rows of staples are installed in an anatomical structure with the structure being cut between the rows. The reader is directed to the following US Patents for further background on the features and uses of exemplary endostaplers of this nature, with the contents of these patents being incorporated by reference into this document: U.S. Pat. Nos. 7,097,089; 7,143,924; 7,398,908; 7,401,721; 7,407,075; 7,472,816; 7,588,174; 7,635,074; 7,753,246; 7,828,189; 7,837,079; 7,845,535; 7,866,525; 7,896,214; 7,967,178; 7,988,028; 7,997,469; 8,011,555; 8,033,438; 8,066,166; 8,157,149; 8,215,532; 8,225,979; 8,292,146; 8,336,753; 8,360,294; 8,360,298; 8,365,972; 8,371,492; 8,397,972; 8,403,195; 8,408,440; 8,418,906; 8,496,153; 8,573,460; 8,579,178; 8,631,989; 8,636,192; 8,684,247; 8,770,458; and 8,777,082.

When endoscopic staplers are used to cut and join anatomical structures having passages therein, the staples often fail to fully join the stapled tissue and close the passages. As an example, use of an endostapler on a pancreas often fails to fully close the main pancreatic duct and/or associated ducts, leading to leakage of pancreatic juice. Pancreatic leakage prolongs patient recovery time and costs, and carries a significantly greater risk of complications (e.g., pancreatitis) and morbidity.

SUMMARY OF THE INVENTION

The invention, which is defined by the claims set forth at the end of this document, is directed to an endoscopic stapler which at least partially alleviates the aforementioned problem. The following brief summary of the invention describes features of preferred versions of the endoscopic stapler, with more details being provided elsewhere in this document. To assist in the reader's understanding, the following review makes reference to the accompanying drawings (which are briefly reviewed in the "Brief Description of the Drawings" section following this Summary section of this document).

Referring initially to FIGS. 1A and 2A, the endoscopic stapler 100 includes a stapler body 102 configured for grasping by an operator's hand to manipulate and operate the stapler 100. First and second stapler units 104a and 104b are distally situated on the stapler body 102. The first stapler unit 104a has opposing elongated first unit upper and lower jaws 108a and 110a, each of which is pivotable with respect to the stapler body 102 about a stapler unit pivot axis (e.g., pivot fastener 106t of FIG. 2C for upper jaw 108a, and pivot fastener 106b of FIG. 2A for lower jaw 110a) to allow the jaws 108a and 110a to pivot between a stowed position (FIG. 1A) wherein the jaws 108a and 110a are axially aligned with the stapler body 102, and a deployed position (FIG. 2A) wherein the jaws 108a and 110a extend outwardly from the axis of the stapler body 102. Likewise, the second stapler unit 104b has opposing elongated first unit upper and lower jaws 108b and 110b which are pivotable with respect to the stapler body 102 (e.g., also at pivot fastener 106t of FIG. 2C for upper jaw 108a, and at pivot fastener 106b of FIG. 2A for lower jaw 110b), allowing the second stapler unit jaws 108b and 110b to pivot between a stowed position (FIG. 1A) along the stapler body 102 and a deployed position (FIG. 2A) angled with respect to the axis of the stapler body 102.

At least one of the first stapler unit upper and lower jaws 108a and 110a is also pivotable about a first unit jaw pivot axis (here with the first unit upper jaw 108a being pivotable about hinge pin 120) to allow the pivotable jaw(s) 108a and/or 110a to swing toward (and away from) the other of the jaws 108a and 110a (compare FIGS. 2A and 3A). Likewise, the second stapler unit 104b has opposing elongated second unit upper and lower jaws 108b and 110b, at least one of which is pivotable about a second unit jaw pivot axis (with the second unit upper jaw 108b here also being pivotable about hinge pin 120). Here too the pivotable jaw(s) 108b and/or 110b can therefore swing toward and away from the other of the jaws 108b and 110b, as also seen in FIGS. 2A and 3A. In each of the stapler units 104a and 104b, one of the upper and lower jaws 108a/110a and 108b/110b is configured to eject staples toward the other of the upper and lower jaws, with the lower jaws 110a/110b here being so configured. Additionally, one of the upper and lower jaws 108a/110a and 108b/110b bears a blade thereon which can be actuated to extend toward, or which can always extend toward, the other of the upper and lower jaws (with the lower jaws 110a and 110b seen in FIG. 2A with blade channels 112a and 112b through which blades 114a and 114b—partially seen in FIG. 7—may be actuated to extend).

This arrangement allows the stapler body 102 to be inserted within a body to be operated upon, with the first and second stapler units 104a and 104b pivoted into their stowed positions (FIG. 1A) for ease of insertion. As the endoscopic stapler 100 approaches the organ or tissue of interest, the first and second stapler units 104a and 104b can be pivoted into their deployed positions of FIG. 2A (also FIG. 3A), at which the lengths of the stapler unit jaws 108a/110a and 108b/110b are preferably oriented at an angle of at least 60 degrees with respect to each other (each preferably being oriented at least 30 degrees from the axis of the stapler body 102). At the same time or otherwise, the jaws 108a/110a and 108b/110b can be opened such that the organ/tissue can be received between the jaws as the stapler body 102 is further advanced toward the organ/tissue. The organ/tissue can then be cut and stapled between the jaws 108a/110a and 108b/110b. The ability to pivot the first and second stapler units 104a and 104b from stowed positions (FIG. 1A) into deployed positions (FIGS. 2A/3A) allows the endoscopic stapler to maintain a small profile during insertion and advancement, and following deployment, allows a larger cut to be made along a direction oriented approximately perpendicular to the axis of the endoscopic stapler 100. Additionally, the ability to pivot the first and second stapler units 104a and 104b into deployed positions wherein their jaws 108a/110a and 108b/110b are oriented in a V-shape allows the endoscopic stapler 100 to make a V-shaped cut, which is particularly useful for operations on the pancreas. This cut shape reconstitutes the original tapered shape of the main pancreatic duct in a single firing (i.e., without needing to reposition and refire the stapler). In contrast, forming this cut shape with prior staplers requires that the stapler be fired, repositioned, and again fired, with a risk of imprecision and resulting pancreatic juice leakage.

The staple-ejecting jaws of the first and second stapler units 104a and 104b—here the lower jaws 110a and 110b—are each preferably configured to eject the staples in two parallel adjacent rows 116a/118a and 116b/118b on each side of the blade channel 112a/112b (and thus each side of the blade 114a/114b therein). Each row contains a spaced array of staples, and the staples within the first row 116a/116b are offset from those in the second row 118a/118b, preferably such that the staples in one of the rows are adjacent the spaces between the staples in the other of the rows. By staggering the staples in this manner, any ducts within the resected organ/tissue that lead to the cut are more likely to be sealed.

The endoscopic stapler 100 also preferably includes a third stapler unit 122 distally situated on the stapler body 102, and which has opposing upper and lower third stapler unit jaws 124 and 126. At least one of the upper and lower jaws 124 and 126 is pivotable about a third stapler jaw pivot axis to pivot within a third unit jaw pivot plane toward (and away from) the other of the upper and lower third stapler unit jaws (compare FIGS. 1A and 2A), with the upper jaw 124 here pivoting about pin 120 with respect to lower jaw 126. One of the upper and lower third stapler unit jaws (here lower jaw 126) is configured to eject staples toward the other of the upper and lower third stapler unit jaws. When the first and second stapler units 104a and 104b are pivoted about their stapler unit pivot axes 106b and 106t into the stowed position of FIG. 1A, they are situated between the upper and lower third stapler unit jaws 124 and 126, again allowing for easier insertion and advancement of the endoscopic stapler 100 within a body. When the first stapler unit jaws 108a and 110a, second stapler unit jaws 108b and 110b, and third stapler unit jaws 124 and 126 are open (FIG. 2A) and they are advanced toward an organ or other tissue, the organ/tissue may be received between the third stapler unit jaws 124 and 126 as well as the first and second stapler unit jaws 108a/110a and 108b/110b. The first and second stapler unit jaws 108a/110a and 108b/110b may then close about and cut and staple the organ/tissue as described above, with the third stapler unit jaws 124 and 126 likewise approaching the organ/tissue (FIG. 3A). At least one of the third stapler unit upper and lower jaws is translatable within the third unit jaw pivot plane toward the other of the third unit upper and lower jaws, allowing the third stapler unit upper and lower jaws 124 and 126 to more firmly close about the organ/tissue. The third stapler unit 122, more particularly the third stapler unit lower jaw 126, may then eject staples into the portion of the organ/tissue that was not cut away by the first and second unit jaws 108a/110a and 108b/110b. Such stapling of the tissue at locations away from the cut edge of the tissue is useful where the endoscopic stapler 100 is used to operate on a pancreas, as the staples applied to the remaining body of the pancreas serve to reduce the flow of pancreatic juice therein, further reducing the chance of pancreatic juice leakage at the cut and stapled edge of the pancreas.

Further potential advantages, features, and objectives of the invention will be apparent from the remainder of this document in conjunction with the associated drawings.

BRIEF DESCRIPTION OF THE DRAWINGS

FIG. 1A is an isometric view of an exemplary version of the endostapler 100, shown with its first stapler unit 104a and second stapler unit 104b in their stowed positions within the third stapler unit 122 (also shown in its stowed position), whereby the endostapler 100 is ready for insertion into and advancement within a body.

FIG. 2A is an isometric view of the endostapler 100 of FIG. 1A, shown with its first stapler unit 104a, second stapler unit 104b, and third stapler unit 122 in their deployed positions whereby an organ or other tissue may be received within their jaws.

FIG. 2C is an isometric view of the endostapler 100 of FIG. 2A shown from a different angle.

FIG. 3A is an isometric view of the endostapler 100 of FIG. 1A, shown with the first stapler unit jaws 108a/110a and second stapler unit jaws 108b/110b pivoted into their closed positions to cut and staple any organ or other tissue therebetween, and with the third stapler unit jaws 124 and 126 likewise pivoted into a partially closed position.

FIG. 3B is a partial sectional isometric view of the endostapler 100 of FIG. 3A, shown with a portion of the stapler body 102 removed to illustrate the components therein.

FIG. 4A is an isometric view of the endostapler 100 of FIG. 1A, shown with the jaws 124 and 126 of the third stapler unit 122 translated into their closed position whereby they can eject staples into any organ/tissue therebetween.

FIG. 4B is a partial sectional isometric view of the endostapler 100 of FIG. 3A, shown with a portion of the stapler body 102 removed to illustrate the components therein.

FIG. 6 is a schematic view illustrating the placement of staples ejected by the first stapler unit 104a and second stapler unit 104b into an organ or other tissue, with the staples being situated about a cut made by the first stapler unit 104a and second stapler unit 104b, showing the staples arrayed in interfit V-shaped paths wherein the staples within each row are offset from the staples in adjacent rows.

FIG. 7 is an enlarged view of portions of the lower jaws of the first stapler unit and second stapler unit, showing the beginning of staple ejection in the dual rows of staplers on opposing sides of the cutting blade (shown emerging from the blade channel between the sets of dual rows).

DETAILED DESCRIPTION OF EXEMPLARY VERSIONS OF THE INVENTION

Figure 1B:
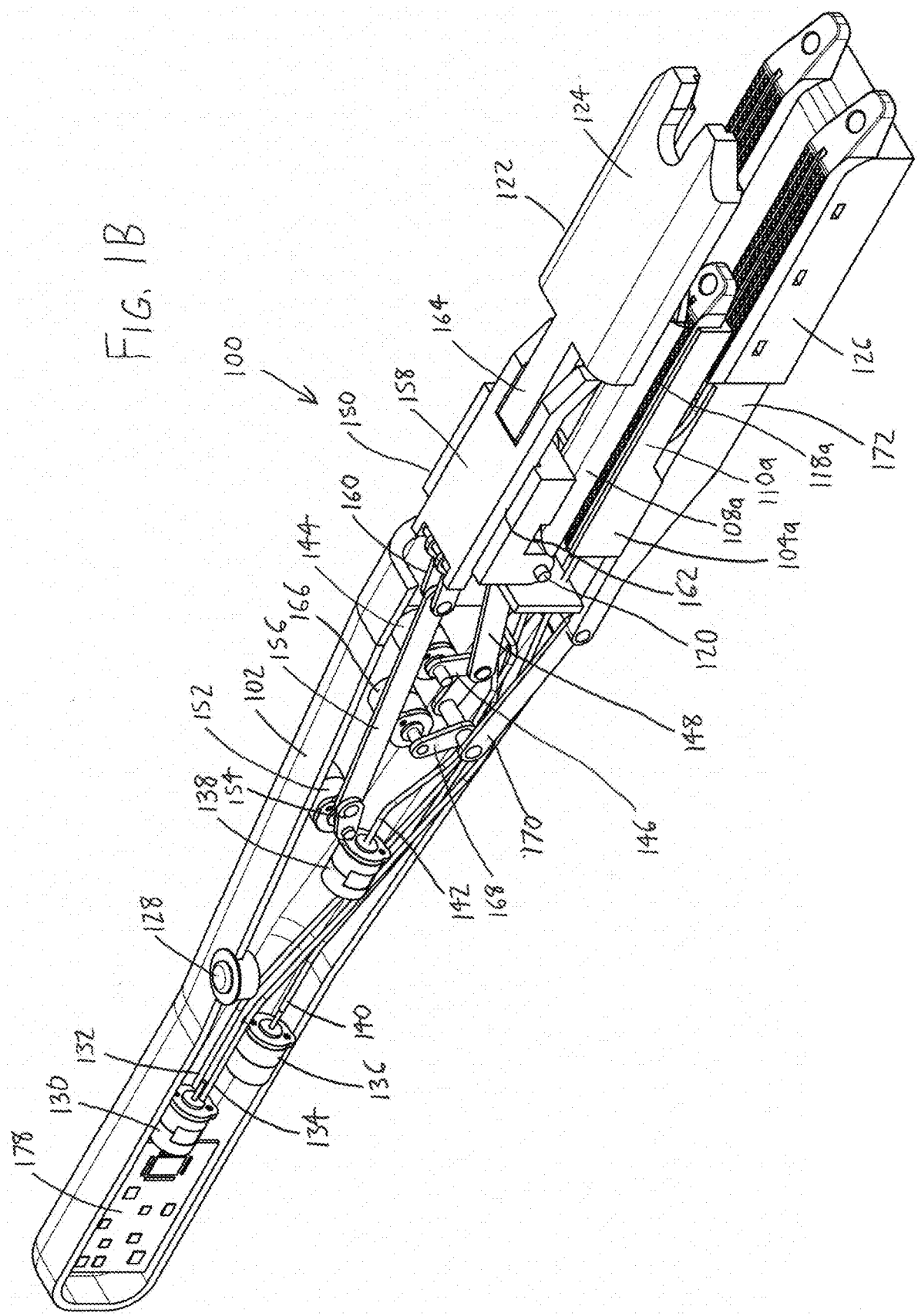
FIG. 1B is a partial sectional isometric view of the endostapler 100 of FIG. 1A, shown with a portion of the stapler body 102 removed to illustrate the components therein.

To again briefly review the operation of the endoscopic stapler 100, FIG. 1A shows the endoscopic stapler 100 ready for grasping by a user along the stapler body 102, and for insertion of the stapler units 104a, 104b, and 122 into a body for advancement toward the organ/tissue to be operated upon. When the first and second stapler units 104a and 104a are in their stowed positions as shown, and nested within the third stapler unit 122, the endoscopic stapler 100 has a smaller diameter and provides lesser resistance to insertion and advancement of the stapler units within the body. Once inserted, the various aforementioned stapler jaw opening, stapler jaw closing, cutting, and stapling functions may be actuated by use of control button 128. During insertion, guidance of the stapler 100 to its desired destination can be assisted by ultrasound or other imaging methods.

Figure 2B:
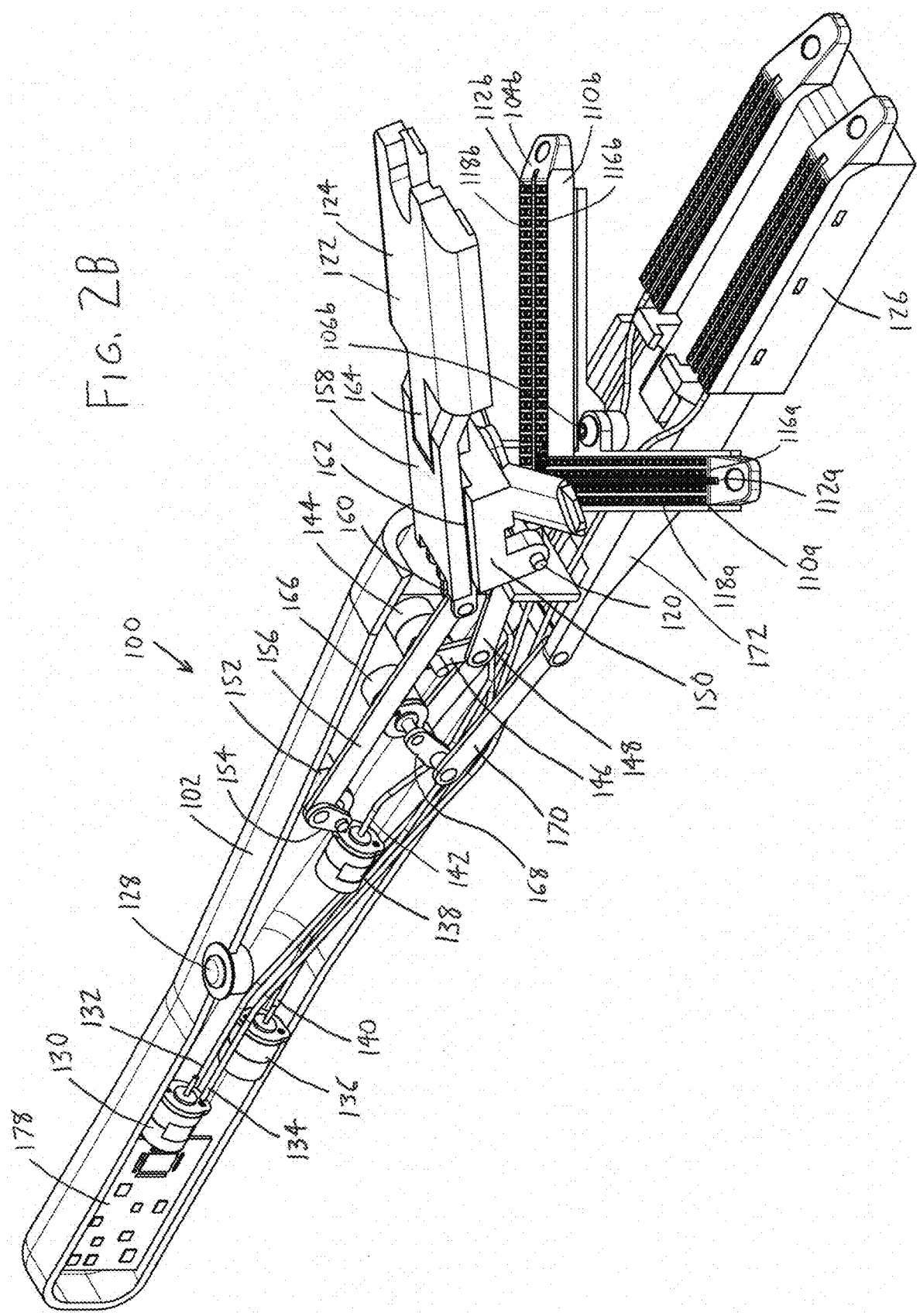
FIG. 2B is a partial sectional isometric view of the endostapler 100 of FIG. 2A, shown with a portion of the stapler body 102 removed to illustrate the components therein.

FIG. 2A then shows the endostapler 100 with its first stapler unit 104*a*, second stapler unit 104*b*, and third stapler unit 122 in their deployed (fully open) positions, whereby they may receive an organ or other tissue therein for cutting and stapling. A user need not fully deploy/open the various jaws of the stapler units, and a user can open them to any extent useful for receiving the target organ/tissue.

FIG. 3A then depicts the upper jaws 108*a* and 108*b* of the first and second stapler units 104*a* and 104*b* pivoted toward the lower jaws 110*a* and 100*b* to grasp, and cut and/or staple, any tissue therebetween. The user may actuate the first and second stapler unit blades 114*a* and 114*b* (FIG. 7) within the lower jaws 110*a* and 110*b* to cut tissue, and/or actuate the staplers in the lower jaws 110*a* and 110*b* to apply rows of staples to the regions of the tissue adjacent the cut. The applied staples may be biodegradable or permanent in accordance with the objectives of the operation being performed with the stapler.

FIG. 4A then illustrates the upper jaw 124 of the third stapler unit 122 translated downwardly toward the third stapler unit lower jaw 126, and thus onto the unresected portion of any organ/tissue between the jaws 124/126. The user may then actuate the stapler in the third stapler unit lower jaw 126 to apply staples to this tissue. As noted above, such application of staples to the unresected portion of the organ/tissue can deter leakage of fluids from the cut. This benefit is particularly valuable in the case of the pancreas, where leakage of pancreatic fluid carries a high risk of complications.

Once the foregoing operations are completed, the jaws 108*a*/110*a* of the first stapler unit 104*a*, the jaws 108*b* and 110*b* of the second stapler unit 104*b*, and the jaws 124 and 126 of the third stapler unit may be partially or entirely opened (FIG. 2A) and sufficiently withdrawn to release the tissue. The first stapler unit 104*a*, second stapler unit 104*b*, and third stapler unit 122 may then be set to their stowed positions for ease of retraction of the endostapler 100, and the endostapler 100 may be withdrawn from the body.

Figure 5:
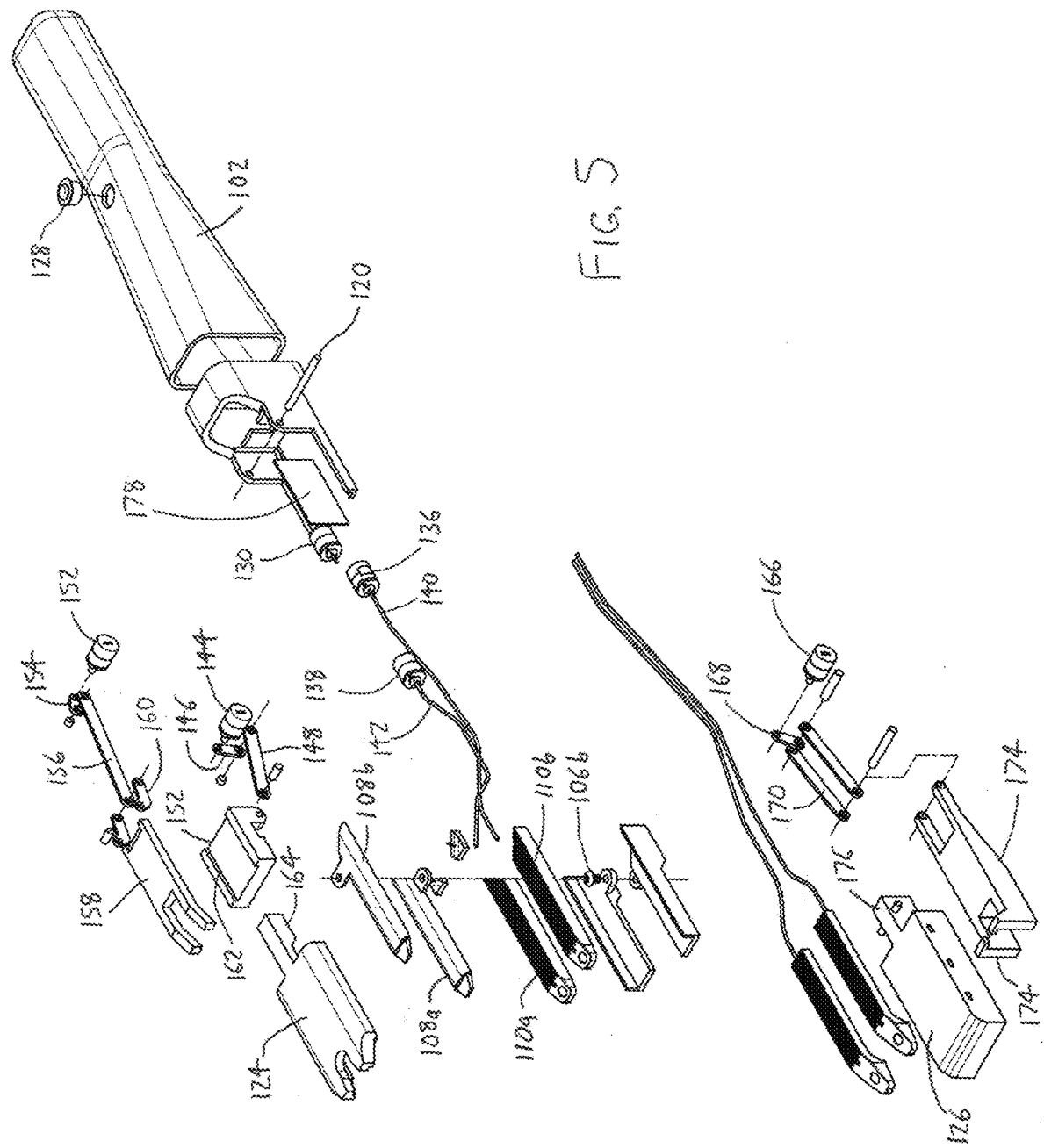
FIG. 5 is an exploded (disassembled) view of the endostapler 100 of FIGS. 1A, 2A, 3A, and 4A, further illustrating the components therein.

Exemplary mechanisms for achieving the aforementioned operations will now be described with reference to any of FIGS. 1B, 2B, 3B, and 4B, in conjunction with FIG. 5. It should be understood that any alternative mechanisms suitable for achieving the operations could be used.

Actuator 130 actuates the deployment of the first and second stapler units 104*a* and 104*b* from their axially-oriented position (as in FIG. 1B) to their V-shaped spread position (as in FIG. 3B) via tension or slack on members 132 and 134. The members 132 and 134 are resiliently flexible, and the actuator 130 can apply tension by spooling/winding the members 132/134, by pulling the members 132/134 via solenoid action, or by any other suitable action.

Actuators 136 and 138 respectively actuate the extension of the first stapler unit blade 114*a* and the second stapler unit blade 114*b* from their respective blade channels 112*a* and 112*b*, and ejection of staples from the first stapler unit lower jaw 110*a* and the second stapler unit lower jaw 110*b*, via tension or slack on members 140 and 142. Referring to FIG. 7, tension on members 140 and 142 actuates respective sliders (not shown) within the respective lower jaws 110*a* and 110*b* which push the blades 114*a* and 114*b* from the channels 112*a* and 112*b*, and which sequentially eject the staples, starting from the vertex of the V at which the lower jaws 110*a* and 110*b* abut when in their V-shaped spread position.

Actuator 144 controls the upward and downward pivoting of the upper jaws 108*a* and 108*b* of the first and second stapler units 104*a* and 104*b* with respect to the lower jaws 110*a* and 110*b*. Rotary output from actuator 144 turns crank arm 146, urging pivotally connected crank arm 148 forwardly or rearwardly. The opposite end of crank arm 148 is pivotally connected to a downwardly-extending leg (not shown) at the bottom of hinge mount 150, which is pivotally pinned to the housing by hinge pin 120 as seen in FIG. 1A. Thus, the forward/rearward motion of crank arm 148 pivots hinge mount 150 upwardly/downwardly about hinge pin 120. The first and second stapler unit upper jaws 108*a* and 108*b* are pivotally connected to the underside of hinge mount 150 via pivot fastener 106*t* (FIG. 2C), and thus pivot with the hinge mount 150.

Actuator 152 actuates upward and downward translation of the upper jaw 124 of the third stapler unit 122 between the positions shown in FIG. 3B and FIG. 4B. Actuator 152 acts on crank arms 154 and 156, which are pivotally linked to fork 158 by arms 160, whereby fork 158 extends or retracts within a channel 160 atop the hinge mount 150. The upper jaw 124 has a rearwardly-extending tail 162 which is received within the fork 158, and which has a ramped lower surface which rides on a pin extending between the arms of the fork 158. Retraction of the fork 158 therefore moves the third stapler unit upper jaw 124 downwardly (FIG. 4B), whereas extension of the fork moves the third stapler unit upper jaw 124 upwardly (FIG. 3B).

In a similar manner, actuator 164 actuates upward and downward translation of the lower jaw of the third stapler unit 122 between the positions shown in FIG. 3B and FIG. 4B. Actuator 164 acts on crank arm 166 to extend or retract crank arms 168, which are pivotally linked to a slider carriage 170 having a ramped bottom. The forward end of slider carriage 170 bears a yoke 172 into which a tail 174 of the third stapler unit lower jaw 126 is received. When the actuator 164 retracts crank arms 168, the ramped bottom of slider carriage 170 rides against the floor of the housing of the endostapler 100, causing it (and the third stapler unit lower jaw 126) to move toward the third stapler unit upper jaw 124. Conversely, extension of the crank arms 168 moves the third stapler unit lower jaw 126 away from the third stapler unit upper jaw 124.

FIG. 6 then illustrates the preferred stapler pattern resulting from ejection of staples from the lower jaws 110*a* and 110*b* of the first and second stapler units 104*a* and 104*b*, which are depicted in greater detail in FIG. 7. On each side of the cut, an outer staple row 118*a*/118*b* is spaced from the blade channel 112*a*/112*b* by an inner staple row 116*a*/116*b*, with all staple rows extending parallel to the blade channel 112*a*/112*b*. The staples in the outer rows 118*a*/118*b* are offset with respect to the staples in the inner row 116*a*/116*b*, i.e., along axes oriented perpendicular to the cut, the ends of the staples are offset, preferably such that the staples within one of the inner and outer rows are primarily aligned with the inter-staple spaces within the other of the rows. This arrangement is more likely to ensure that any ducts within the tissue that extend to the cut will be closed by a staple.

The stapler pattern provided by the first and second stapler unit lower jaws 110*a* and 110*b* need not also be provided in the staplers of the lower jaw 126 of the third stapler unit 122, which might simply provide staple rows wherein the staples are aligned rather than offset, or may provide other patterns in single or multiple rows. Looking to FIG. 2C, the staplers 180 of the third stapler unit lower jaw 126 are situated on opposing sides of, and are raised with respect to, a central valley 182 on the third stapler unit lower jaw 126. The third stapler unit upper jaw 124 is similarly configured, having spaced anvils 184 with a valley 186 therebetween. The valleys 182 and 186 avoid compression of the central pancreatic duct as the staplers 180 apply staples to the duct's opposing sides.

The stapler need not take the form described and shown, and numerous modifications are possible. As examples, the configuration of the first and second stapler units 104a and 104b can be varied from those shown; for example, their jaws 108a/110a and 108b/110b need not be linear, and might be curved such that a curved cut and curved rows of staples are applied. The staplers can be provided on the opposite jaws of one or other of, or both of, the first/second stapler units 104a/104b and the third stapler unit 122. The third stapler unit 122 can be omitted if the endostapler 100 need not apply such additional staples. Additionally, the configuration of the third stapler unit 122, and the number and placement of its staples, could be varied from the depicted arrangement (e.g., it might apply additional rows of staples oriented parallel to those applied by the first and second stapler units 104a and 104b). The control button 128 is merely an exemplary control interface, and other interfaces are possible (e.g., multi-button interfaces, lever/slide controls, etc.). Likewise, the stapler body 102 can be differently dimensioned or configured; in particular, it might terminate slightly rearwardly from the stapler units 104a, 104b, and 122, at which point it may bear an attachment interface allowing attachment (and control connection to) a chosen handle/manipulator.

Various terms referring to orientation and position are used throughout this document, such as "upper" (as in "first unit upper jaw") and "lower" (as in "first unit lower jaw"), and such terms should be understood to be relative terms rather than absolute ones. In other words, it should be understood (for example) that the first unit upper jaw may in fact be located at the bottom of the apparatus (or elsewhere) depending on the overall orientation of the apparatus. Thus, such terms should be regarded as words of convenience, rather than limiting terms. Additionally, when it is said that jaws are pivotable with respect to each other, this should be understood to mean that one jaw may pivot toward the other (stationary) jaw, or each jaw may be pivotable toward the other.

Throughout this document, when it is said that an axis (or plane) is oriented perpendicular to another axis (or plane), this should be understood as encompassing the situation where the stated axes/planes are oriented perpendicularly but do not intersect, as well as the situation where the stated axes/planes are perpendicular and intersecting. Further, where it is said that axes or planes are "substantially" perpendicular, this should be understood as meaning within ten degrees of perpendicular; likewise, where it is said that axes or planes are "substantially" parallel, this should be understood as meaning within ten degrees of parallel.

The version of the invention described above is merely exemplary, and the invention is not intended to be limited to this version. Rather, the scope of rights to the invention is limited only by the claims set out below, and the invention encompasses all different versions that fall literally or equivalently within the scope of these claims. In these claims, no element therein should be interpreted as a "means-plus-function" element or a "step-plus-function" element pursuant to 35 U.S.C. § 112(f) unless the words "means for" or "step for" are explicitly used in the particular element in question.

What is claimed is:

1. An endoscopic stapler including:
   a. a stapler body,
   b. first and second stapler units, each:
      (1) being configured to pivot with respect to the stapler body, and
      (2) having opposing elongated upper and lower jaws configured to pivot with respect to each other, wherein:
         (a) one of the upper and lower jaws is configured to eject staples toward the other of the upper and lower jaws, and
         (b) one of the upper and lower jaws bears a blade thereon extending toward the other of the upper and lower jaws.

2. The endoscopic stapler of claim 1 wherein:
   a. the first and second stapler units are configured to pivot with respect to the stapler body about a stapler pivot axis, and
   b. the upper and lower jaws of the first and second stapler units are configured to pivot with respect to each other about a jaw pivot axis oriented at least substantially perpendicular to the stapler unit pivot axis.

3. The endoscopic stapler of claim 1 wherein each jaw configured to eject staples is further configured to eject the staples:
   a. spaced in an array along a first row, and
   b. spaced in an array along a second row adjacent and parallel to the first row,
   wherein the staples within the first and second rows are offset such that the staples in one of the rows are adjacent the spaces between the staples in the other of the rows.

4. The endoscopic stapler of claim 1 wherein:
   a. the first and second stapler units are configured to pivot with respect to the stapler body into a deployed position wherein the lengths of the upper and lower jaws of the first stapler unit are oriented at least 60 degrees from the lengths of the upper and lower jaws of the second stapler unit,
   b. each jaw configured to eject staples is further configured to eject the staples in a row oriented along the length of the jaw, whereby the ejected staples of the jaws are arrayed along a V-shaped path when the first and second stapler units are in the deployed position.

5. The endoscopic stapler of claim 1 wherein:
   a. the first and second stapler units are configured to pivot with respect to the stapler body into a deployed position wherein the lengths of the upper and lower jaws of the first stapler unit are oriented at least 60 degrees from the lengths of the upper and lower jaws of the second stapler unit,
   b. each jaw configured to eject staples is further configured to eject the staples:
      (1) spaced in an array along a first row, and
      (2) spaced in an array along a second row adjacent and parallel to the first row, whereby the ejected staples of the jaws are arrayed in interfit V-shaped paths when the first and second stapler units are in the deployed position.

6. The endoscopic stapler of claim 1 further including a third stapler unit having opposing upper and lower third stapler unit jaws configured to pivot with respect to each other, wherein:
   a. at least a portion of each of the first and second stapler units is situated between the upper and lower third stapler unit jaws, b. one of the upper and lower third stapler unit jaws is configured to eject staples toward the other of the upper and lower third stapler unit jaws.

7. The endoscopic stapler of claim 6 wherein the first and second stapler units are configured to pivot with respect to the stapler body into a stowed location wherein the lengths of the upper and lower jaws of the first stapler unit are at least substantially parallel to the lengths of the upper and lower jaws of the second stapler unit.

8. The endoscopic stapler of claim 6 wherein the first and second stapler units are configured to pivot with respect to the stapler body out of, and entirely into, a volume about which the upper and lower third stapler unit jaws pivot.

9. The endoscopic stapler of claim 6 wherein at least one of the upper and lower third stapler unit jaws is translatable toward the other of the upper and lower third stapler unit jaws.

10. The endoscopic stapler of claim 6 wherein at least one of the upper and lower third stapler unit jaws includes a pair of staplers thereon wherein the staplers are spaced by a depressed region therebetween.

11. An endoscopic stapler including:
  a. a stapler body,
  b. a first stapler unit:
    (1) being pivotable with respect to the stapler body within a stapler unit pivot plane,
    (2) having opposing first unit upper and lower jaws, at least one of the first unit upper and lower jaws being pivotable within a first unit jaw pivot plane toward the other of the first unit upper and lower jaws, wherein:
      (a) one of the first unit upper and lower jaws is configured to eject staples toward the other of the first unit upper and lower jaws, and
      (b) one of the first unit upper and lower jaws bears a blade thereon extending toward the other of the first unit upper and lower jaws,
  c. a second stapler unit:
    (1) being pivotable with respect to the stapler body within the stapler unit pivot plane,
    (2) having opposing second unit upper and lower jaws, at least one of the second unit upper and lower jaws being pivotable within a second unit jaw pivot plane toward the other of the second unit upper and lower jaws, wherein:
      (a) one of the second unit upper and lower jaws is configured to eject staples toward the other of the second unit upper and lower jaws, and
      (b) one of the second unit upper and lower jaws bears a blade thereon extending toward the other of the second unit upper and lower jaws,
  wherein the first unit jaw pivot plane and second unit jaw pivot plane are oriented at least substantially perpendicular to the stapler unit pivot plane.

12. The endoscopic stapler of claim 11 wherein each jaw configured to eject staples is further configured to eject the staples:
  a. spaced in an array along a first row, and
  b. spaced in an array along a second row adjacent and parallel to the first row,
  wherein the staples within the first and second rows are offset such that a line:
  (1) from each space between each staple in the second row,
  (2) oriented perpendicular from the second row, intersects a respective staple in the first row.

13. The endoscopic stapler of claim 11 wherein:
  a. the first and second stapler units are pivotable within the stapler unit pivot plane into a deployed position wherein the upper and lower jaws of the first stapler unit are oriented at least 60 degrees from the upper and lower jaws of the second stapler unit,
  b. each jaw configured to eject staples is further configured to eject the staples in a row, whereby the ejected staples of the jaws are arrayed along a V-shaped path when the first and second stapler units are in the deployed position.

14. The endoscopic stapler of claim 11 wherein:
  a. the first and second stapler units are pivotable within the stapler unit pivot plane into a deployed position wherein the upper and lower jaws of the first stapler unit are oriented at least 60 degrees from the upper and lower jaws of the second stapler unit,
  b. each jaw configured to eject staples is further configured to eject the staples:
    (1) spaced in an array along a first row, and
    (2) spaced in an array along a second row adjacent and parallel to the first row, whereby the ejected staples of the jaws are arrayed in interfit V-shaped paths when the first and second stapler units are in the deployed position.

15. The endoscopic stapler of claim 11 further including a third stapler unit:
  a. having opposing third unit upper and lower jaws, at least one of the third unit upper and lower jaws being pivotable within a third unit jaw pivot plane toward the other of the third unit upper and lower jaws,
  b. wherein one of the third unit upper and lower jaws is configured to eject staples toward the other of the upper and lower third stapler unit jaws.

16. The endoscopic stapler of claim 15 wherein the third unit jaw pivot plane intersects the stapler unit pivot plane.

17. The endoscopic stapler of claim 15 wherein the first and second stapler units are pivotable within the stapler unit pivot plane into and out of a volume about which the at least one of the third unit upper and lower jaws pivot toward the other of the third unit upper and lower jaws.

18. The endoscopic stapler of claim 15 wherein the first and second stapler units are pivotable within the stapler unit pivot plane into a stowed location wherein the first and second stapler units are situated between the upper and lower third stapler unit jaws.

19. The endoscopic stapler of claim 15 wherein at least one of the third unit upper and lower jaws is translatable within the third unit jaw pivot plane toward the other of the third unit upper and lower jaws.

20. An endoscopic stapler including:
  a. a stapler body,
  b. a first stapler unit:
    (1) pivotable with respect to the stapler body about a first stapler unit pivot axis,
    (2) having opposing first unit upper and lower jaws pivotable with respect to each other about a first jaw pivot axis, wherein:
      (a) one of the first unit upper and lower jaws is configured to eject staples toward the other of the first unit upper and lower jaws, and
      (b) one of the first unit upper and lower jaws bears a blade thereon extending toward the other of the first unit upper and lower jaws, c. a second stapler unit:
  (1) pivotable with respect to the stapler body about a second stapler unit pivot axis,
  (2) having opposing second unit upper and lower jaws pivotable with respect to each other about a second jaw pivot axis, wherein:
    (a) one of the second unit upper and lower jaws is configured to eject staples toward the other of the second unit upper and lower jaws, and
    (b) one of the second unit upper and lower jaws bears a blade thereon extending toward the other of the second unit upper and lower jaws,
wherein:
A. the first stapler unit pivot axis and the second stapler unit pivot axis are situated in a common stapler unit pivot plane,
B. the first jaw pivot axis and second jaw pivot axis are situated in a common jaw pivot plane oriented at least substantially perpendicular to the common stapler unit pivot plane.

\* \* \* \* \*